United States Patent [19]

Higo et al.

[11] 4,383,052

[45] May 10, 1983

[54] 1-METHACRYLOXYETHANE-1,1-DIPHOSPHONIC ACID AND ITS SALTS AND DENTAL ADHESIVE COMPOSITION CONTAINING SAME

[75] Inventors: Moriaki Higo; Yasuo Kikuchi, both of Ninomiya; Shinya Kitoh, Hiratsuka; Shin-ichi Suzuki; Haruhiko Toda, both of Odawara, all of Japan

[73] Assignee: Lion Corporation, Tokyo, Japan

[21] Appl. No.: 330,604

[22] Filed: Dec. 14, 1981

[30] Foreign Application Priority Data

Dec. 20, 1980 [JP] Japan .............................. 55-181063

[51] Int. Cl.$^3$ .......................... C08K 5/10; C08K 5/50
[52] U.S. Cl. .................................................... 523/118
[58] Field of Search ............................... 523/118, 109; 260/998.11; 560/222; 433/217, 228

[56] References Cited

U.S. PATENT DOCUMENTS 3,766,252 10/1973 Schmidt et al. ..................... 560/222
4,259,075 3/1981 Yamauchi et al. ............. 260/998.11

Primary Examiner—John Kight, III
Assistant Examiner—Amelia B. Yarbrough
Attorney, Agent, or Firm—Birch, Stewart, Kolasch & Birch

[57] ABSTRACT

A novel compound, 1-methacryloxyethane-1,1-diphosphonic acid and its salts provide improved adhesion to tooth substances when used as a polymerizable monomer in a dental adhesive composition.

9 Claims, No Drawings

1-METHACRYLOXYETHANE-1,1-DIPHOSPHONIC ACID AND ITS SALTS AND DENTAL ADHESIVE COMPOSITION CONTAINING SAME

BACKGROUND OF THE INVENTION

This invention relates to a novel compound, 1-methacryloxyethane-1,1-diphosphonic acid and its salts, used as a polymerizable monomer in a dental adhesive composition.

For the treatment of dental caries, composite resins were developed as a substitute for conventional dental cements such as zinc phosphate cement and silicate cement. Recently, improved composite resins are available which are to be stable for a prolonged period of time, because of reduced water-absorption and degradation, and exhibit very little difference in color from natural teeth.

However, since composite resins do not essentially adhere to tooth enamel or dentin, there is a likelihood that a gap will be formed between tooth cavity and composite resin embedded therein over a long period of time. Such a gap tends to facilitate secondary caries and eventually a filled composite resin will fall from the cavity.

To improve the adhesion between the composite resin and the cavity wall, a variety of adhesion promotors or adhesive liners were developed. Also proposed were adhesive caries-preventive filling materials, maligned tooth orthodontic adhesives, and other dental adhesive compositions which solely aim at firm adhesion to tooth substances. Most of them have problems with respect to durability in the mouth and ease of handling and few materials can firmly adhere to tooth for a long period of time in a wet, temperature-varying environment like the mouth.

SUMMARY OF THE INVENTION

Making extensive investigations for a compound which has increased adhesion to tooth and is advantageously used as a polymerizable monomer in a dental adhesive composition, the inventors have discovered a novel compound, 1-methacryloxyethane-1,1-diphosphonic acid having the formula (1) and its salts

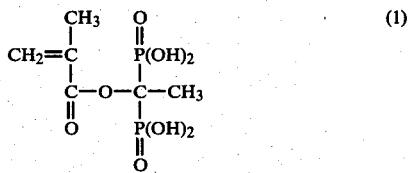

which may be prepared, for example, by reacting methacryloyl chloride with 1-hydroxyethane-1,1-diphosphonic acid. According to the inventors' findings, cured products obtained by polymerizing or curing the compound of formula (1) or its salts show increased adhesion to tooth even in water. Polymers of the compound of formula (1) or copolymers of the compound of formula (1) with other monomers, when used as a dental filling material, firmly adhere to a tooth cavity wall so that neither formulation of a gap nor falling of the filling material due to poor adhesion will occur, and when used as a primer or adhesive for a filling material such as a composite resin, provide improved marginal sealing so that secondary caries is effectively prevented. All these features demonstrated that the compound of formula (1) and its salts may be advantageously used as a polymerizable monomer in a dental adhesive composition.

It is, therefore, an object of the present invention to provide a novel compound of formula (1) and its salts which are used as a polymerizable monomer in a dental adhesive composition.

It is another object of the present invention to provide a dental adhesive composition which comprises at least one compound selected from the group consisting of a novel compound of formula (1) and its salts which is used for the purpose of adhesion to tooth.

These and other objects, features and advantages of the present invention will become apparent from the following description.

DETAILED DESCRIPTION OF THE INVENTION

The novel compound, 1-methacryloxyethane-1,1-diphosphonic acid of the present invention is a water-soluble colorless oily substance having the chemical structure represented by formula (1) mentioned above and the infrared absorption and NMR spectra to be described later.

This novel compound of formula (1) may be prepared in accordance with the general processes for the synthesis of esters as described in the literature, for example, "Jikken Kagaku Koza (Experimental Chemistry Lecture)," Vol. 19, pages 471–482 (MARUZEN CO., LTD., May 20, 1957) and "Shin Jikken Kagaku Koza (New Experimental Chemistry Lecture)," Vol. 14, pages 1000–1062 (MARUZEN CO., LTD., Oct. 20, 1975), for example, by reacting methacrylic acid with 1-hydroxyethane-1,1-diphosphonic acid or methacrylic acid anhydride with 1-hydroxyethane-1,1-diphosphonic acid. Most preferably, the compound may be prepared by reacting methacryloyl halide such as methacryloyl chloride with 1-hydroxyethane-1,1-diphosphonic acid in an anhydrous condition in the presence of a base with cooling.

Salts of the novel compound of formula (1) are obtained by replacing all or some of the hydrogen atoms in the hydroxyl groups of the compound of formula (1) by metal substituents or amines. The salts include alkali metal salts such as lithium salt, sodium salt and potassium salt, alkali earth metal salts such as magnesium salt and calcium salt, ammonium salt, primary, secondary and tertiary amine salts such as cyclohexyl ammonium salt, and double salts thereof. The salts may be prepared by neutralizing the compound of formula (1) with a metal or ammonium carbonate solution, adding a solvent such as ethanol, and filtering the solution to collect the precipitate, i.e. the salt of the compound of formula (1). The salts may also be prepared by reacting methacrylic acid or its derivatives such as methacryloyl chloride with a salt of 1-hydroxyethane-1,1-diphosphonic acid. Moreover, the compound of formula (1) may be converted into alkali metal or alkaline earth metal salts as by reacting the compound of formula (1) with a corresponding metal, metal oxide or metal hydroxide or treating it with an ion exchange resin bearing a corresponding metal. The novel compound of formula (1) may also be converted into the ammonium salt or primary, secondary or tertiary amine salts as by reacting the compound with ammonia, ammonium hydroxide or a primary, secondary or tertiary amine or treating it with an ion exchange resin of the (substituted) ammonium type.

The compounds of the present invention may be used as polymerizable monomer in a dental adhesive composition of the type where the polymerizable monomer is polymerized upon use. The compound of formula (1) and its salts may be used either alone as a sole polymerizable monomer or in admixture with any desired other polymerizable monomers. The compound of formula (1) and its salts may be polymerized or cured into homopolymers or copolymers with other monomers, which can firmly adhere to tooth.

Dental adhesive compositions containing the compound of formula (1) or its salts may be used for the purpose of adhesion to tooth. The composition may be used as a filling material or an orthodontic adhesive. The composition may also be used as a primer or undercoat for assisting in adhering a filling material such as a composite resin or an orthodontic adhesive to tooth.

When the compound of formula (1) or its salts are used as a polymerizable monomer in a dental adhesive composition, the composition may contain any additional ingredients generally used for such a purpose although the actual choice of ingredients depends on the type and intended use of a particular composition.

When a dental adhesive composition is used as an adhesive filling material, the compound of formula (1) or its salts may be a sole polymerizable monomer which may be polymerized or cured in the presence of a curing agent into a cured material applicable as an adhesive filling material. Preferably, the dental adhesive composition used as the adhesive filling material comprises a mixture of the compound of formula (1) or its salts and other polymerizable monomers, which may be polymerized or cured in the presence of a curing agent upon use.

The other monomers which can be used in combination with the compound of formula (1) or its salts may be mono- or polyfunctional groups. Examples of the monofunctional and polyfunctional monomers are enumerated below.

Monofunctional Monomer
    methyl acrylate and methacrylate,
    ethyl acrylate and methacrylate,
    butyl acrylate and methacrylate,
    allyl acrylate and methacrylate,
    hydroxyethyl acrylate and methacrylate,
    methoxyethyl acrylate and methacrylate,
    glycidyl acrylate and methacrylate,
    tetrahydrofurfuryl acrylate and methacrylate, styrene, etc.

Polyfunctional Monomer
Difunctional aliphatic acrylate and methacrylate
    ethylene glycol diacrylate and dimethacrylate,
    diethylene glycol diacrylate and dimethacrylate,
    triethylene glycol diacrylate and dimethacrylate,
    tetraethylene glycol diacrylate and dimethacrylate,
    polyethylene glycol diacrylate and dimethacrylate,
    butylene glycol diacrylate and dimethacrylate,
    neopentyl glycol diacrylate and dimethacrylate,
    propylene glycol diacrylate and dimethacrylate,
    1,3-butanediol diacrylate and dimethacrylate,
    1,4-butanediol diacrylate and dimethacrylate,
    1,6-hexanediol diacrylate and dimethacrylate, etc.

Difunctional aromatic acrylate and methacrylate
    2,2-bis(acryloxyphenyl)propane,
    2,2-bis(methacryloxyphenyl)propane,
    2,2-bis(4-(3-acryloxy)-2-hydroxypropoxyphenyl)propane,
    2,2-bis(4-(3-methacryloxy)-2-hydroxypropoxyphenyl)propane,
    2,2-bis(4-acryloxyethoyphenyl)propane,
    2,2-bis(4-methacryloxyethoxyphenyl)propane,
    2,2-bis(4-acryloxydiethoxyphenyl)propane,
    2,2-bis(4-methacryloxydiethoxyphenyl)proane,
    2,2-bis(4-acryloxytriethoxyphenyl)propane,
    2,2-bis(4-methacryloxytriethoxyphenyl)propane,
    2,2-bis(4-acryloxytetraethoxyphenyl)propane,
    2,2-bis(4-methacryloxytetraethoxyphenyl)propane,
    2,2-bis(4-acryloxypentaethoxyphenyl)propane,
    2,2-bis(4-methacryloxypentaethoxyphenyl)propane,
    2,2-bis(4-acryloxybutoxyphenyl)propane,
    2,2-bis(4-methacryloxybutoxyphenyl)propane,
    2,2-bis(4-acryloxydibutoxyphenyl)propane,
    2,2-bis(4-methacryloxydibutoxyphenyl)propane,
    2,2-bis(4-acryloxydipropoxyphenyl)propane,
    2,2-bis(4-methacryloxydipropoxyphenyl)propane,
    2,2-bis(4-acryloxytripropoxyphenyl)propane,
    2,2-bis(4-methacryloxytripropoxyphenyl)propane,
    2-(4-acryloxyethoxyphenyl)-2-(4-acryloxydiethoxyphenyl)propane,
    2-(4-methacryloxyethoxyphenyl)-2-(4-methacryloxydiethoxyphenyl)propane,
    2-(4-acryloxydiethoxyphenyl)-2-(4-acryloxytriethoxyphenyl)propane,
    2-(4-methacryloxydiethoxyphenyl)-2-(4-methacryloxytriethoxyphenyl)propane,
    2-(4-acryloxydipropoxyphenyl)-2-(4-acryloxytriethoxyphenyl)propane,
    2-(4-methacryloxydipropoxyphenyl)-2-(4-methacryloxytriethoxyphenyl)propane,
    2,2-bis(4-acryloxypropoxyphenyl)propane,
    2,2-bis(4-methacryloxypropoxyphenyl)propane,
    2,2-bis(4-acryloxyisopropoxyphenyl)propane,
    2,2-bis(4-methacryloxyisopropoxyphenyl)propane,
    xylylene glycol diacrylate,
    xylylene glycol dimethacrylate,
    bis(ethyleneoxide)bisphenol-A diacrylate and methacrylate, etc.

Trifunctional aliphatic acrylate and methacrylate
    trimethylolpropane triacrylate and trimethacrylate,
    trimethylolethane triacrylate and trimethacrylate,
    trimethylolethanol triacrylate and trimethacrylate,
    trimethylolmethane triacrylate and trimethacrylate,
    pentaerythritol triacrylate and trimethacrylate, etc.

Tetrafunctional acrylate and methacrylate
    tetramethylolmethane tetraacrylate and tetramethacrylate, etc.

In the adhesive filling material, oligomers and polymers may be blended in an amount of 0–30% by weight of the polymerizable monomers with the above-mentioned monomers for the purpose of regulating viscosity, curing rate and curing shrinkage. The oligomers and polymers include those of the compound of formula (1) and its salts, methyl acrylate, methyl methacrylate, hydroxyethyl acrylate, hydroxyethyl methacrylate, tetrahydrofurfuryl acrylate, tetrahydrofurfuryl methacrylate, glycidyl acrylate, glycidyl methacrylate, styrene, and the like.

Also included are fillers which serve to increase the compressive strength, hardness and other physical properties of a cured product. Inorganic fillers ae usually employed although organic fillers may be employed to improve surface gloss of a cured product and the affinity or bonding with polymerizable monomers.

The inorganic fillers include alpha-quartz, fumed silica, glass beads, aluminum oxide, and the like. The particle size is not particularly limited although fillers having a particle size of less than 100 microns, especially less than 50 microns are preferred. Those fillers having a particle size as small as several microns or less are also preferred to increase surface smoothness. Also included is a combination of particles having a size of several ten microns and particles having a size of several microns. The inorganic fillers may preferably be pretreated with a silane coupling agent in order to obtain an improved bonding with monomers. Examples of the silane coupling agent for such pretreatment are vinyl trichlorosilane, vinyl triethoxysilane, vinyl trimethoxysilane, vinyl tris($\beta$-methoxyethoxy)silane, $\gamma$-methacryloxypropyl trimethoxysilane, N-($\beta$-aminoethyl)-$\gamma$-aminopropyl trimethoxysilane, and the like. The organic fillers which can be employed herein are those prepared by finely dividing a polymer of any of the above-mentioned monomers to a particle size of less than 50 microns in a ball mill or any suitable means. Another procedure to prepare organic fillers is polymerization of monomers dispersing inorganic fillers having a particle size of less than 10 microns. The polymerization cured product is finely divided to a particle size of less than 50 microns in a ball mill or any suitable means. It is to be noted that the filler may be blended in an amount of 50–85% by weight of the total weight of a filling material.

Polymerization inhibitors, coloring agents, antioxidants and other well-known ingredients may be blended.

Catalysts or curing agents may also be blended in the filling material. Any suitable known catalysts or curing agents may be used, for example, a combination of an amine and a peroxide, or sulfinic acid or its derivatives and a peroxide. When the compound of formula (1) or its salts are sole polymerizable monomers, the monomer may be divided into two equal parts. One part contains a first curing agent, for example, an amine or p-toluene sulfinic acid and the other part contains a second curing agent, for example, a peroxide. When the compound of formula (1) or its salts are to be mixed with other polymerizable monomers, the other monomers may be divided into two equal parts. One part contains a first curing agent and the other part contains a second curing agent. The compound of formula (1) or its salts may be added to either or both of the two parts, which are to be mixed upon use. In both cases, other additional ingredients may be added to either or both of the two parts. Immediately before application, these two parts are blended into a mixture which will cure by nature. The amine may include N,N-dimethyl-p-toluidine, N,N'-di($\beta$-hydroxyethyl)-p-toluidine, N,N-dimethyl aniline, monoethanol amine and the like. The content of the amine may preferably be in the range of from 0.1 to 5% by weight of the polymerizable monomers. Derivatives of sulfinic acid may be benzene sulfinic acid, p-toluene sulfinic acid and their sodium salts, and the like. The content of sulfinic acid or its derivatives may preferably be in the range of from 2 to 6% by weight of the polymerizable monomers. The peroxide may include benzoyl peroxide, di-p-chloro-benzoyl peroxide, di-lauroyl peroxide, methyl ethyl ketone peroxide and the like. The content of the peroxide may preferably be in the range of from 0.1 to 3% by weight of the polymeriable monomers.

The filling material may also be formulated into an ultraviolet curable system by blending an ultraviolet sensitizer such as benzoin methyl ether, acetophenone, benzophenone, 2,2,2-trichloro-4'-t-buthylacetophenone, anthraquinone and the like in an amount of 0.3–3% by weight of the monomers. In this case, all the necessary ingredients may be blended into a single composition which must be packed in a UV-shielded package.

The compound of formula (1) or its salts may be blended in varying, unlimited amounts in the adhesive filling material. When the compound of formula (1) or its salts are used in combination with other polymerizable monomers as described above, the compound of formula (1) or its salts may preferably be 1–30% by weight, particularly 2–15% by weight based on the other polymerizable monomer. Poor adhesion results from amounts of less than 1% whereas cured products have sometimes reduced hardness with amounts of more than 30%. It is to be noted that the adhesive filling material may preferably comprise 10–45% by weight of a polymerizable monomer or monomers and 50–85% by weight of an inorganic filler.

When a dental adhesive composition containing the compound of formula (1) or its salts used as an adhesive for adhering a conventional filling material such as a composite resin to tooth, this composition may be prepared by adding 1–15% by weight of the compound of formula (1) or its salts to a suitable organic solvent such as ethanol, diethyl ether and chloroform preferably at a concentration of 0.5–30% by weight. Another preferred composition may be prepared by mixing 1–15% by weight of the composition of the compound of formula (1) or its salts with other polymerizable monomers. The mixture may be dissolved into a suitable solvent. A further preferred composition may be prepared by using the same formulation as described for the adhesive filling material. It should be noted that improved adhesion cannot be achieved when the compound of formula (1) or its salts are present in extremely smaller or larger proportions.

These dental adhesive compositions may be applied or cured in a manner depending on their type and intended use. When the composition is used as a filling material, this adhesive composition or filling material may be introduced into a cavity to be filled and then cured in situ. When the composition is used for the purpose of adhesion of a dental filling material to tooth, this adhesive composition may be applied to the wall of a cavity to be filled before the cavity is filled with a desired filling material which is then cured in situ.

Dental adhesive compositions containing the compound of formula (1) or its salts according to the present invention can maintain a high degree of adhesion even in water or saliva because a polymer of the compound of formula (1) or its salts has improved adhesion to tooth substances. The compositions are highly durable in the mouth. When the composition is used as a filling material, it firmly adheres to a tooth for a long period of time even in wet, temperature-varying environment as in the mouth. When the composition is used for the purpose of adhesion as a primer or undercoat for a composite resin or orthodontic adhesive, it firmly adheres to tooth as well as to the composite resin or orthodontic adhesive and prevents a gap from forming between tooth and the composite resin or orthodontic adhesive, thereby providing sufficient marginal sealing to control secondary caries.

The examples of the present invention are set forth below by way of illustration and not by way of limitation.

EXAMPLE 1

To 5 g (0.024 mol) of 1-hydroxyethane-1,1-diphosphonic acid in 30 ml of triethylamine was gradually added 15.7 g (0.15 mol) of methacryloyl chloride with ice cooling. After the temperature was raised to room temperature, the mixture was stirred for ten hours. The reaction solution was acidified with aqueous hydrochloric acid and then extracted with diethyl ether. The resulting aqueous phase was alkalized with sodium hydroxide and then extracted again with diethyl ether. The resulting aqueous phase was chromatographed over Amberlite 120B (trade mark, Rohm & Haas Co.) and the solvent of the eluate was evaporated to give 4.3 g of a colorless oily substance which was identified to be 1-methacryloxyethane-1,1-diphosphonic acid (yield 65%).

Elemental analysis for $C_6H_{12}O_8P_2$:
Calculated: C 26.29%, H 4.41%, P 22.60%, Found: C 26.55%, H 4.19%, P 22.35%.

Infrared absorption spectrum: $\nu_{max}^{NaCl}$

| | |
|---|---|
| 2700 cm$^{-1}$ | P—OH |
| 1720 | O—C—C= ‖ O |
| 1450 | CH$_3$— |
| 1380 | CH$_3$— |
| 1200 | P—OH ‖ O |

NMR spectrum: in d$_6$-DMSO

| | |
|---|---|
| 6.85 ppm b.s. | (4H, —P(OH)$_2$) |
| 5.93 m | (1H, —C(=O)O—, C=C, CH$_3$, H, H) |
| 5.48 m | (1H, —C(=O)O—, C=C, CH$_3$, H, H) |
| 1.82 m | (3H, —C(=O)O—, C=CH$_2$, CH$_3$) |
| 1.44 t | (3H, O=P—(OH)$_2$, CH$_3$—C—, O=P—(OH)$_2$) J = 15 Hz |

1-Methacryloxyethane-1,1-diphosphonic acid was thermally polymerized at about 150° C.

Metal salts of 1-methacryloxyethane-1,1-diphosphonic acid shown in Tables 1 and 2 were prepared by adding a corresponding metal carbonate solution to 1-methacryloxyethane-1,1-diphosphonic acid at a molar ratio of 1:1, adding ethanol to the mixture, and filtering the solution to collect the precipitate (the metal salt).

Cyclohexyl ammonium salt was also prepared by adding 1 mole of cyclohexylamine to 1 mole of 1-methacryloxyethane-1,1-diphosphonic acid, agitating the mixture, and fractionating the reaction product by liquid chromatography to obtain the salt.

The infrared absorption and NMR spectra of the salts are shown in Tables 1 and 2.

The melting point of cyclohexyl ammonium salt was 177°–181° C.

TABLE 1

| | IR($\nu_{max}^{NaCl}$) | | | | |
|---|---|---|---|---|---|
| Salt | —P(=O)—(OM)$_2$ | —O—C(=O)—C= | CH$_3$— | CH$_2$= | —NH$_3^+$ |
| lithium salt | 3550 cm$^{-1}$ | 1690 cm$^{-1}$ | 1385 cm$^{-1}$ 1450 | 2890 cm$^{-1}$ | |
| sodium salt | 3300 | 1700 | 1450 1380 | | |
| potassium salt | 3300 | 1710 | 1450 1340 | 2950 | |
| magnesium salt | 3400 | 1700 | 1450 | 2900 | |
| ammonium salt | 3400 | 1700 | 1430 | | |
| cyclohexyl ammonium salt | 2850 | 1700 | 1460 | | 3200 cm$^{-1}$ 1580 |

TABLE 2

NMR($\delta$ in D$_2$O)

| Salt | 1H $-\underset{\underset{CH_3}{|}}{\overset{\overset{O}{\|}}{C}}\diagdown_{O}C=C\diagup^{H}_{H}$ | 1H $-\underset{\underset{CH_3}{|}}{\overset{\overset{O}{\|}}{C}}\diagdown_{O}C=C\diagup^{H}_{H}$ | 3H $-\underset{\underset{CH_3}{|}}{\overset{\overset{O}{\|}}{C}}\diagdown_{O}C=CH_2$ | 3H $CH_3-\underset{\underset{O=P-(OH)_2}{|}}{\overset{\overset{O=P-(OH)_2}{|}}{C}}-$ | $\left(NH_3^+-\hspace{-2pt}\bigcirc\hspace{-6pt}\diagup^{H}\right)_4$ | $\left(\begin{array}{c}H\diagup^{H}\hspace{-2pt}H\diagdown_{H}\\H-\hspace{-6pt}\bigcirc\hspace{-6pt}-H\\H\diagdown_{H}\hspace{-2pt}H\diagup^{H}\end{array}\right)_4$ |
|---|---|---|---|---|---|---|
| lithium salt | m 6.00 | m 5.58 | m 1.91 | t J = 14 Hz 1.81 | | |
| sodium salt | m 6.02 | m 5.51 | m 1.81 | t J = 14 Hz 1.78 | | |
| potassium salt | m 6.03 | m 5.51 | m 1.83 | t J = 14 Hz 1.80 | | |
| magnesium salt | m 6.09 | m 5.63 | m 1.91 | t J = 14 Hz 1.71 | | |
| ammonium salt | m 5.98 | m 5.53 | m 1.86 | t J = 13 Hz 1.78 | | |
| cyclohexyl ammonium salt | m 6.05 | m 5.43 | m 1.90 | t J = 14 Hz 1.86 | m 2.98 | m 1.23 |

In the following examples, application of the compound of the present invention to tooth substances is illustrated. All parts and percentages are by weight.

EXAMPLE 2

A primer or dental adhesive composition was prepared by dissolving the compound of formula (1) in ethanol at a concentration of 5%.

A bovine tooth embedded in a holder with a gypsum binder and an acrylic rod (6 mm diameter, 40 mm long) were finished so as to have a given degree of surface smoothness by means of a polisher. The finished surface of the bovine tooth was treated with 3 M phosphoric acid for 30 seconds, rinsed with water for 30 minutes, and then dried with compressed-air blast. The above-prepared primer was applied to the dried tooth surface and dried before the acrylic rod was attached thereto using an adhesive polymer of the following formulation. The assembly was stored in artificial saliva at a temperature of 37° C. After storage for 14 and 60 days, adhesion was measured using a Strograph at a pulling rate of 5 mm/min. The results are shown in Table 3.

| Formulation of the adhesive polymer | | |
|---|---|---|
| | | Part by weight |
| (a) | Methyl methacrylate | 2 |
| | Polymethyl methacrylate | 0.4 |
| | N,N—dimethyl-p-toluidine | 0.04 |
| (b) | Methyl methacrylate | 2 |
| | Polymethyl methacrylate | 0.4 |
| | Benzoyl peroxide | 0.04 |

Portions (a) and (b) were mixed at a weight ratio of 1:1 immediately before application.

TABLE 3

| | Bond strength kg/cm$^2$ | |
|---|---|---|
| | 14 days | 60 days |
| Present compound (1) | 98 | 92 |

As seen from Table 1, the compound of formula (1) according to the present invention maintains its increased bond strength over prolonged periods.

EXAMPLE 3

A mixture was prepared by thoroughly mixing 10 parts of methyl methacrylate, 20 parts of diethylene glycol dimethacrylate, 50 parts of bisphenol-A diglycidyl methacrylate and 350 parts of silane-coupled quartz sand having a particle size of less than 50 microns, and divided into two equal portions. Then 6 parts of the compound of formula (1) and 2 parts of N,N-dimethyl-p-toluidine were added to one portion, while 2 parts of benzoyl peroxide was added to the other portion. These two portions were mixed together. Using the resulting mixture, an acrylic rod was attached to a bovine tooth at their smoothly finished surfaces in the same manner as in Example 2. Using the Strograph, the adhesion was measured to be 64 kg/cm$^2$ (average) after one week storage in water.

EXAMPLE 4

A cavity having a diameter of 4 mm and a depth of 2-2.5 mm was prepared in an extracted human tooth at the labial surface. The cavity wall was etched with 3 M phosphoric acid for 30 seconds. A solution consisting of 10 parts of the compound of formula (1), 60 parts of methyl methacrylate and 30 parts of tetraethylene glycol dimethacrylate was then applied to the etched wall of the cavity, which was filled with Adaptic (trade mark, manufactured by Johnson & Johnson Co.). After the thus filled tooth was allowed to stand for 30 minutes for curing, it was immersed in water at a temperature of 37° C. for one day. Thereafter, the tooth was subjected to a percolation test in which the tooth sample was alternately dipped in aqueous Fuchsine solutions at 4° C. and 60° C. each for one minute and 60 times for each solution. This percolation test was designed to examine marginal sealing. The tooth was cut at the center into two to examine at the cross section whether or not the dyestuff (Fuchsine) had penetrated between the cavity wall and the filling material. No penetration of the dyestuff was observed.

When a tooth cavity was filled with Adaptic without pre-treatment with the solution containing the compound of the present invention, it was found that the dyestuff (Fuchsine) had penetrated along the cavity wall to the dentinal portion or to the cavity floor. These results prove that the compound of the present invention is also effective for adhesion between the tooth and a filling material.

What is claimed is:

1. 1-Methacryloxyethane-1,1-diphosphonic acid having the formula (1) and its salts.

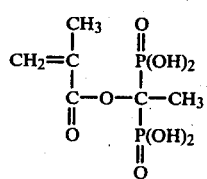

(1)

2. A dental adhesive composition comprising at least one compound selected from the group consisting of 1-methacryloxyethane-1,1-diphosphonic acid having the formula (1) and its salts.

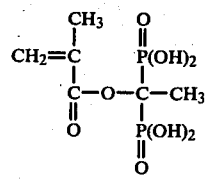

(1)

3. The composition according to claim 2, wherein said compound of the formula (1) or a salt thereof is present in said composition in an amount of 1–15% by weight.

4. The composition according to claim 2, wherein said compound of the formula (1) or a salt thereof is present in said composition in combination with another polymerizable monomer in an amount of 1–30% by weight based on the other polymerizable monomer.

5. The composition according to claim 4, wherein said compound of the formula (1) or a salt thereof is present in said composition in an amount of 2–15% by weight based on the other polymerizable monomer.

6. The composition according to claim 2, which comprises 10–45% by weight of a polymerizable monomer or monomers.

7. The composition according to claim 3, which comprises 10–45% by weight of a polymerizable monomer or monomers.

8. The composition according to claim 4, which comprises 10–45% by weight of a polymerizable monomer or monomers.

9. The composition according to claim 2, which comprises 50–85% by weight of an inorganic filler.

* * * * *